United States Patent [19]
Buinevicius et al.

[11] Patent Number: 5,179,952
[45] Date of Patent: Jan. 19, 1993

[54] ELECTROCARDIAL STIMULATOR PROBE
[75] Inventors: Rimas P. Buinevicius, Palos Park; William Metzger, Libertyville, both of Ill.
[73] Assignee: Arzco Medical Electronics Inc., Vernon Hills, Ill.
[21] Appl. No.: 566,745
[22] Filed: Aug. 13, 1990
[51] Int. Cl.⁵ .............. A61B 5/0402; A61N 1/05
[52] U.S. Cl. .................. 128/642; 128/715; 128/784
[58] Field of Search .......... 128/642, 670, 671, 715, 128/773, 784

[56] References Cited

U.S. PATENT DOCUMENTS

| | | |
|---|---|---|
| Re. 31,377 | 9/1983 | Mylrea et al. |
| 3,081,765 | 3/1963 | Kompelien |
| 3,480,003 | 11/1969 | Crites |
| 3,499,435 | 3/1970 | Rockwell et al. |
| 3,533,403 | 10/1970 | Woodson |
| 3,568,660 | 3/1971 | Crites et al. |
| 3,734,094 | 5/1973 | Calinog |
| 3,951,136 | 4/1976 | Wall |
| 4,088,138 | 5/1978 | Diack et al. |
| 4,090,518 | 5/1978 | Elam |
| 4,176,660 | 12/1979 | Mylrea et al. |
| 4,198,963 | 4/1980 | Barkalow et al. |
| 4,301,809 | 11/1981 | Pinchak |
| 4,304,239 | 12/1981 | Perlin |
| 4,304,240 | 12/1981 | Perlin |
| 4,319,580 | 3/1982 | Colley et al. |
| 4,331,156 | 5/1982 | Apple et al. |
| 4,349,031 | 9/1982 | Perlin |
| 4,351,330 | 9/1982 | Scarberry |
| 4,383,534 | 5/1983 | Peters |
| 4,409,986 | 10/1983 | Apple et al. |
| 4,475,555 | 10/1984 | Linder |
| 4,476,872 | 10/1984 | Perlin |
| 4,517,984 | 5/1985 | Perlin |
| 4,519,403 | 5/1985 | Dickhudt |
| 4,574,807 | 3/1986 | Hewson et al. |
| 4,577,638 | 3/1986 | Graham |
| 4,607,643 | 8/1986 | Bell et al. |
| 4,619,268 | 10/1986 | Uphold et al. |
| 4,640,298 | 2/1987 | Pless et al. |
| 4,658,836 | 4/1987 | Turner |
| 4,671,295 | 6/1987 | Abrams et al. |
| 4,683,890 | 8/1987 | Hewson |
| 4,706,681 | 11/1987 | Breyer et al. |
| 4,706,688 | 11/1987 | Don Michael et al. |
| 4,722,347 | 2/1988 | Abrams et al. |
| 4,735,206 | 4/1988 | Hewson |
| 4,763,660 | 8/1988 | Kroll et al. |
| 4,817,611 | 4/1989 | Arzbaecher et al. |
| 4,852,580 | 8/1989 | Wood |
| 4,890,623 | 1/1990 | Cook et al. |
| 4,960,133 | 10/1990 | Hewson .......... 128/642 X |

FOREIGN PATENT DOCUMENTS

| | | |
|---|---|---|
| 121090 | 2/1972 | Denmark . |
| 0101595 | 2/1984 | European Pat. Off. ........ 128/642 |
| 2003138 | 7/1971 | Fed. Rep. of Germany . |
| 133400 | 1/1979 | Fed. Rep. of Germany . |
| 2135196 | 8/1984 | United Kingdom ........ 128/642 |

OTHER PUBLICATIONS

Chapter 11, *Temporary Cardiac Pacing*, Jadvar and Arzbaecher "Temporary Esophageal Pacing".
An article entitled "A Pill Electrode For The Study of Cardiac Arrhythmia" by Arzbaecher, published in 1978 in the Journal Medical Instrument.
An article entitled "Use of the Pill Electrode For Transesophageal Atrial Pacing" by Jenkins et al. published in the Journal PACE in 1985.

*Primary Examiner*—Lee S. Cohen
*Attorney, Agent, or Firm*—Dressler, Goldsmith, Shore, Sutker & Milnamow

[57] ABSTRACT

A probe for electrocardial stimulation includes a catheter-like conduit for insertion into a patient's esophagus. The conduit has openings which are spaced apart at two longitudinal locations which are closely adjacent to the patient's heart when the probe is positioned in the esophagus. The openings pick up heart sounds and transmit them to the interior of the conduit for communication to the proximal end of the probe, where they can be monitored by attending personnel. Two electrodes are spaced apart longitudinally between and in fixed relation to the openings, so as to position the electrodes accurately relative to the heart based upon heart sounds transmitted through the openings. Other functions, such as a temperature sensor or stomach feeding or pumping capability may also be provided inside the conduit.

15 Claims, 1 Drawing Sheet

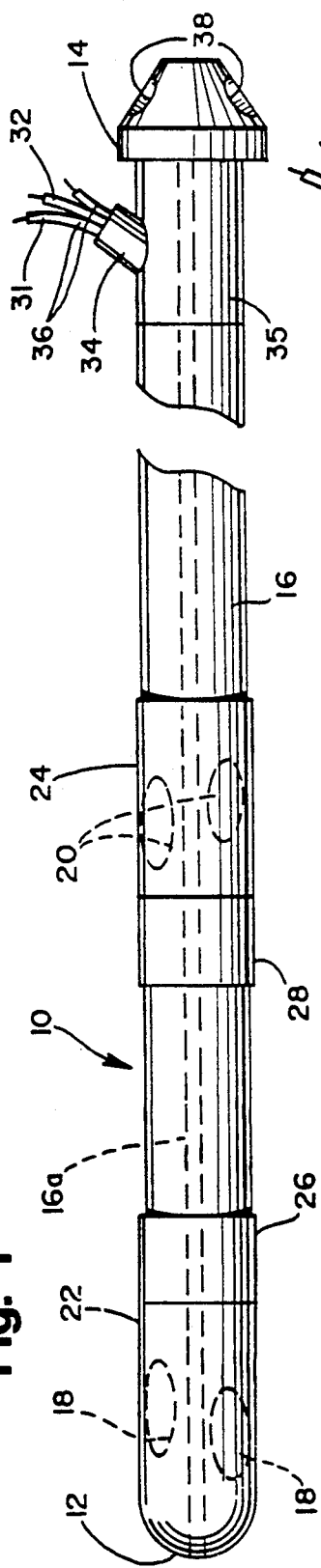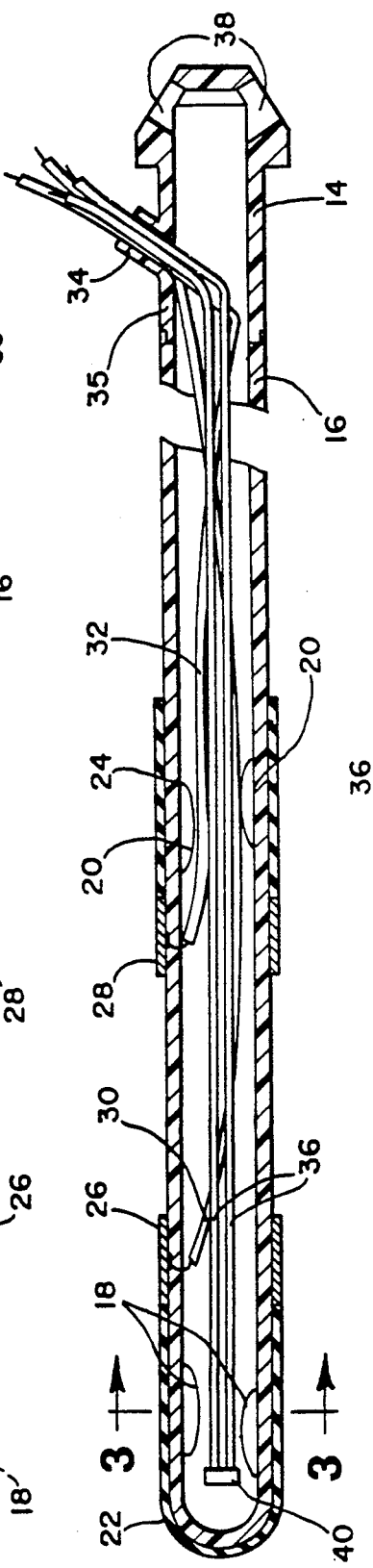

ELECTROCARDIAL STIMULATOR PROBE

FIELD OF THE INVENTION

The invention relates to medical probes for electrically recording and stimulating the heart of a patient.

BACKGROUND OF THE INVENTION

Electrode probes for inserting into a body to record electrical signals from and to stimulate the heart are generally known in the prior art. Such probes are inserted into the body past the pharynx and into the esophagus or trachea into close proximity to the heart. Such probes may be used either for diagnosis or for therapeutic applications. For diagnosis, the heart can be monitored, and for therapeutic purposes, an electrical stimulus applied to the heart via the probe at any instant, as appropriate.

Stethoscopes for monitoring heart sounds are also well-known. The most commonly known type is an external device which consists simply of a pair of ear pieces and a tube leading to each ear piece which transmits heart sounds from a pick-up, which is usually placed in proximity to the heart of the patient. Stethoscope pick-ups for insertion into a patient's esophagus, trachea or pharynx are also known. If inserted into the esophagus, these stethoscopes may be a long hollow tube having a closed distal end and one or more openings positioned along the length of the tube, to transmit heart sounds from inside the esophagus through the interior of the tube. The openings are typically covered with a thin film, which is sealed to the tube, to prevent body fluid from entering the stethoscope. The physician's ear pieces are connected to a Y-cap at the proximal end of the tube, so that the physician can monitor the heart sounds inside the esophagus.

Other types of stethoscopes for insertion through the mouth or nose are also well known. such as ones which use a microphone or other transducer to convert the heart sounds into electrical signals and wires to conduct the electrical signals from the transducer to outside of the patient for monitoring by attending personnel. U.S. Pat. No. 4,088,138 discloses a cardiac resuscitator and monitoring apparatus having an oropharyngeal airway for insertion into the mouth of a patient who has undergone a suspected heart attack. The airway has an electrical micro-phone at its end and electrodes for giving an indication of electrical heart activity. An electrical signal to stimulate the heart, such as a defibrillating or pacing pulse, may be provided between these electrodes or a separate electrode on the airway, and another electrode applied elsewhere to the patient's body.

It is important in such devices to position such active electrodes as closely to the heart as possible. Because the esophagus comes in close proximity to the left atrium, less current is required to pace the heart at this location compared to other locations. This is advantageous for a number of reasons, one of which is the reduced pain and hazard to the patient. Although the current levels required to pace the ventricles are high, it should be understood that such electrodes may also be used for ventrical stimulation in the event of some form of atrio-ventricular block inhibiting the normal conduction pathways of the heart. It is usually intended to apply the signal to the atria, and not the ventricles, to avoid inducing undesired cardiac reactions, such as ventricular fibrillation.

It is also desirable to make probes for insertion into the body as inexpensively as possible so that they can be disposed of after each use rather than requiring sterilization. That way, a new probe can be used for each patient without risk of infection.

SUMMARY OF THE INVENTION

The invention provides an electrocardial stimulator probe which can be accurately positioned relative to a patient's heart, and is inexpensive to produce and therefore disposable after each use. The probe includes a tubular flexible conduit which is sized and shaped for insertion past the patient's pharynx. A distal end of the conduit is inserted into the body first and the conduit extends from the distal end outside of the pharynx to a proximal end to communicate cardiac sounds from inside the body to the proximal end, where they can be monitored. An electrode is fixed on the exterior surface of the conduit for applying an electrical stimulus to the heart of the body and a conductor extends inside the conduit from the electrode to the proximal end for applying the electrical signal to the electrode.

In a preferred form, the conduit has at least one opening formed in its wall. The opening is positioned along the length of the conduit so that the opening can be longitudinally positioned along the length of the esophagus adjacent to the heart of the body to receive through the opening sounds produced by the heart. The electrodes are longitudinally fixed on the exterior of the conduit relative to the longitudinal position of the opening so as to impart an electrical signal to the atrium of the heart when the conduit is moved into position relative to the heart according to heart sounds received through the opening. With this construction, attending personnel can accurately position the opening, and therefore the electrodes, at the desired longitudinal location relative to the heart based on either the heart sounds, transmitted through the opening and monitored at the proximal end of the probe, or based on monitoring of atrial activity using the electrodes themselves.

In an especially useful form, the conduit has at least two openings which are spaced apart longitudinally. The electrodes are positioned longitudinally on the exterior of the conduit between the longitudinal positions of the openings. Heart sounds are communicated through the spaced apart openings and to the proximal end of the probe, to accurately position the electrodes relative to the heart. Preferably, two electrodes are positioned on the exterior of the conduit between the longitudinal positions of the openings and the electrodes and the sets of openings are placed symmetrically relative to each other so that relative placement of one inherently also places the other.

BRIEF DESCRIPTION OF THE DRAWINGS

FIG. 1 is a side elevation view of an electrocardial stimulator probe of the invention.

FIG. 2 is a cross-sectional view taken along the plane of the line 2—2 of FIG. 1.

FIG. 3 is a cross-sectional view taken along the plane of the line 3—3 of FIG. 1.

DETAILED DESCRIPTION OF THE PREFERRED EMBODIMENT

Shown in FIG. 1 is an illustration of an electrocardial stimulator probe 10 constructed in accordance with the present invention. The probe 10 has a closed distal end 12 and an open proximal end 14. A catheter-like cylindrical conduit 16 extends between the distal end 12 and proximal end 14, the distal end 12 forming an integral part of the conduit 16 and having a hemispherical shape for easy insertion into a patient's esophagus. The conduit 16 is made of silicone rubber or other anatomically inert flexible material suitable for body insertion.

The conduit 16 is tubular, having a hollow interior to conduct heart sounds from inside the esophagus to the proximal end 14. The outside diameter of the conduit 16 is suitable for insertion past a patient's pharynx into the esophagus. In the preferred embodiment, the outer diameter of the conduit 16 is 18 French, although conduits anywhere in the range of from 8 to 24 French may be easily used for various patients. The conduit 16 is of thin walled construction, having an internal diameter of any suitable size for conducting heart sounds longitudinally through it to the proximal end 14.

Two sets of openings, distal openings 18 and proximal openings 20, are circumferentially distributed around the conduit 16 at respective longitudinally spaced locations. There may be any suitable number of holes 18 and 20 in each set of openings, and there may be more than two sets of openings in some versions. In the preferred embodiment, there are four distal holes 18 and four proximal holes 20, which are equally spaced around the circumference of the conduit 16. As shown in FIGS. 2 and 3, the holes 18 and 20 extend all the way through the wall of the conduit 16 and are sized to communicate heart sounds from inside the esophagus through the wall of the conduit 16 to the interior of the conduit 16. In the preferred embodiment, the holes 18 are oval having dimensions of about 5 millimeters along their major axes in the longitudinal direction. Within each set of four holes, the holes are grouped in two sets of two. In the preferred arrangement, the holes in each set of two openings are located on the radially opposite side of the conduit from each other, and the two other holes in the set of four are located at a position rotated 90° from the first two holes. In this way there is one hole in each set of openings located generally in each radial direction. In this way the functioning of the openings as sound passages is facilitated since sound may enter from every side. The particular orientation, grouping and location of the openings can be varied as long as the symmetrical placement of the openings relative to the conductors is maintained so that the placement of the conduit by sound will result in proper placement of the electrodes adjacent the heart.

Body fluids, such as gastric juices or other body fluids, are prevented from entering the interior of the conduit 16 through the distal 18 and proximal opening 20 by thin membranes 22 and 24, which cover the openings 18 and 20 and which are impermeable to fluid. These membranes 22 and 24 may be made of silicone rubber, or other anatomically inert material which can be sealed against the conduit 16 to form a fluid tight seal. The membrane 22 is in the shape of a open ended sack, which fits closely over the distal end 12 and covers the openings 18. The membrane 24 is a sleeve, having two open ends, which also fits tightly against conduit 16. The open ends of the sack 22 and sleeve 24 are sealed against the conduit 16 with any appropriate fluid-tight sealing technique, such as RF welding. Stethoscope pick-ups similar to the conduit 16 are commercially available from Electromedics, Inc. of Englewood Colo. Another strategy instead of using the sleeves would be to construct a stethoscope of a single extruded piece of material with thick and thin segments extending through it, with the thin segments serving as the sound passages.

While the preferred construction is illustrated in the drawings, in an alternative construction the openings 18 and 20 could be molded into the conduit 16 with a thin film of the conduit material formed over the opening. The thin film, which would be integral with the conduit 16, would separate the interior of the conduit from the exterior and form an impermeable membrane, in which case the membranes 22 and 24 would be unnecessary. Also, if a probe of the invention was made for insertion into the trachea, modifications to the details of the electrode and opening locations might be appropriate.

Sleeve shaped distal electrodes 26 and proximal electrodes 28 are slipped over the outside of the conduit 16 and membranes 22 and 24 in a friction fit at spaced apart longitudinal locations. The electrodes 26 and 28 are cylinders made of an electrically conductive medically inert material, such as stainless steel. The diametric size of the cylinders of the electrodes 26 and 28 is selected so that the electrodes may be slid onto the exterior of the conduit 16, but will tightly bind to the exterior of the conduit so as to remain in position thereon. As shown in FIG. 2, each of the electrodes 26 and 28 trap and bear against a stripped end of insulated wire conductors 30 and 32, respectively, between the corresponding electrode and the conduit 16. This forms an electrical connection between the wire conductor 30 and the electrode 26 and between the wire conductor 32 and the electrode 28. Thus to assemble the probe, the ends of the wire conductors 30 and 32 only need be stripped bare and inserted in place, with the electrodes then being positioned over them. The frictional grasp of the conduit by the electrodes not only holds the electrodes in place, but also makes electrical contact between the conductors 30 and 32 and the electrodes 26 and 28. It should also be understood that the electrodes could be fixed in location by other means, such as welding, soldering, gluing with conductive epoxy or by placement in a formed channel. Also other methods of attachments for of the conductors to the electrodes are possible.

While the embodiment disclosed has two electrodes, and therefore is bipolar, it should be understood that a unipolar construction having only one electrode could be provided or that more than two electrodes could be provided. In fact, for some applications, more than two electrodes are highly desirable. If the probe is to be used both for monitoring and for stimulation of the heart, the probe would preferably be provided with four electrodes so that there would be two electrodes for monitoring and two for stimulation. Another alternative would be to provide for both ventrical and atrial stimulation and monitoring by providing two electrodes for atrial monitoring or pacing and two electrodes located further down the length of the conduit for ventrical monitoring or pacing. Multiple electrodes may also be provided on a single probe to allow for patients of different size or anatomical structure, with only one set of electrodes normally being used.

It is also envisioned that in versions of the probe in accordance with the present invention, other esophageal functions needed during a surgical procedure may be incorporated into the combined probe. Such functions might include feeding tubes (enteral tubes), 16a illustrated in phantom in FIG. 1, which act to place fluids in the stomach, and sump or lavage tubing which can act to rid the stomach of foreign substances and prevent aspiration during surgery. These functions could be incorporated inside the conduit of the probe described here without interfering with any of the electrocardial monitoring or pacing or stethoscopic operations of the probe.

Holes are drilled or otherwise formed in the conduit 16 at the longitudinal locations of the electrodes 26 and 28, for the wire conductors 30 and 32 to extend from outside conduit 16, through the wall of the conduit 16, to the interior of the conduit. Wires 30 and 32 extend longitudinally through the conduit 16 toward the proximal end 14, and exit through a branch 34 of a Y-cap 35 which forms the proximal end 14 and is secured in a permanent or semi-permanent connection to the conduit 16. The conducting elements could also extend outside of the conduit or within the wall of the conduit to the proximal end of the probe. The Y-cap 35 also provides at the proximal end 14 a pair of holes 38, to which the ear pieces of a stethoscope can be attached so that attending personnel can monitor heart sounds transmitted to the interior of the conduit 16.

In the preferred embodiment illustrated, a pair of wires 36 extends through the branch 34 and through the interior of the conduit 16 to a temperature sensor 40, such as a thermistor, which senses the temperature inside the conduit 16. When the wires 36 are connected to an appropriate temperature read-out device, the temperature inside the conduit 16, and therefore the patient's temperature inside the esophagus, can be monitored. It is also envisioned that other sensors of patient condition can also be placed in the conduit, such as sensors for pH or esophageal pressure. It would also be possible to install microphones or another sound pickup device in the conduit if amplification of the sound from the heart was desired.

The conductors 30 and 32 at their ends outside of the conduit 16 are stripped of insulation for connection to an electrical cardiac stimulating device, such as the pulse generator of a pacemaker or of a defibrillator. Both ends of the conductors are thus outside of the conduit, the distal ends penetrating the conduit to connect to the electrodes, and the proximal ends attached to the external monitoring or pacing equipment. The probe can provide the pick-up of an electronic stethoscope for monitoring heart sounds inside the esophagus, as well as a means for applying electrical stimuli to the heart of the patient.

To apply electrical stimuli for pacing the heart, it is important to apply the stimuli to the atria, and not the ventricles. To do so, the electrodes must be positioned closely adjacent to one or more of the atria. By providing the electrodes 26 and 28 between and closely adjacent to the openings 18 and 20, this can be accomplished using the probe 10.

The conduit 16 is long enough to allow positioning of the openings 18 and 20 in the esophagus closely adjacent to the heart of the patient. Normal hearts make four characteristic sounds known as the first, second, third and fourth heart sounds or cardiac sounds. The first and second sounds are the principal sounds. The first is deeper and longer, and is caused by the contraction of the ventricles (the lower, strong chambers of the heart) and the closure of the valves between the atria and the ventricles. The second sound is shorter and is caused by the closure of the valves between the ventricles and the two large arteries (the aorta and pulmonary artery) by which the blood leaves the ventricles. The third and fourth sounds are less audible. The third sound is caused by the flow of blood into the ventricles. The fourth sound is caused by the contraction of the atria. By listening to these heart sounds transmitted through the openings 18 and 20 into the probe, attending personnel can longitudinally position the probe, and therefore the electrodes, along the length of the esophagus precisely in the desired position relative to the heart.

Another method of positioning the probe is by electrical monitoring. A normal electrocardiograph measured on the surface of the patient exhibits complexes which have been labelled as the P, QRS and T complexes of signals. The P wave corresponds to the depolarization of the atria and is typically small when measured from the skin of the patient. The QRS is the repolarization of the atrium and the depolarization of the ventricles. The T wave is the repolarization of the ventricles. When the same signals are monitored by a probe in the esophagus, the measured P wave is much greater relative to the QRS complex, which is indicative of placement near the atrium. Therefore an alternate method of placing the probe in the esophagus is to connect monitoring, rather than stimulating, equipment to the electrodes and to place the probe at the position with the maximum measured P wave signal. In the electrical mode of placement, the sound passages now benefit from the electrical placement by being inherently now located adjacent the atrium as well.

Thus the symmetrical placement of the sound openings and the electrodes ensures that each one may be properly placed by careful placement of the other of them. In this may the maximum flexibility in the use of the instrument is maintained.

The longitudinal spacing of the openings 18 and 20 and the electrodes 26 and 28 is helpful in allowing accurate positioning of the electrodes 26 and 28 relative to the heart. Preferably, the electrodes 26 and 28 should be positioned in the range of 10 millimeters to 30 millimeters longitudinally apart center to center, and preferably 15 to 25 millimeters center to center. Each of the electrodes 26 and 28 is preferably 5 millimeters long. The openings need tö be placed sufficiently close to the electrodes so that centering the openings by sound also centers the electrodes. Note also that the two sets of openings 18 and 20 are located distally and proximally of the electrodes 26 and 28 so that neither opening is between the electrodes. This arrangement helps to ensure that the electrodes are properly positioned when the probe is inserted, and when the insertion position of the probe is determined by sound, since the electrodes will always be between the location determined by the sounds perceived, rather than outside of it. The electrodes could also be placed just outside of the openings, so long as the symmetrical position of the openings relative to the electrodes is maintained.

The construction of the probe 10 described provides a relatively inexpensive electrocardial stimulator which can be used for accurate positioning of stimulation electrodes relative to the heart in a disposable unit. Although one embodiment of the invention has been described, numerous modifications will be apparent to those of ordinary skill in the art but are still within the spirit and scope of the invention. Therefore, the invention should not be defined as limited to the preferred embodiment illustrated and described, but should be defined by the claims which follow.

We claim:

1. An electrocardial probe insertable into an esophagus of a body with the esophagus located adjacent to a cardiac organ, the probe comprising:
   a tubular, flexible, hollow conduit with an exterior surface, a proximal end and a distal end, said distal end and said conduit are sized and shaped for insertion, at least in part, into the esophagus with said conduit defining an axially extending interior lumen to communicate cardiac sounds from inside the body to said proximal end, said lumen and said exterior surface bounding a conduit wall;
   means, at said proximal end, for communicating sounds inside said hollow conduit to an external listening device;
   at least one electrode carried on said exterior surface usable for one of cardiac monitoring or stimulation;
   a conductor coupled to and extending between said electrode and said proximal end;
   means, at said proximal end, for connecting said conductor to an external source of electrical energy for use in one of cardiac monitoring or stimulation;
   at least two sets of sound transmissive openings formed in said conduit wall, said sets of openings are spaced apart longitudinally along said conduit with said electrode positioned therebetween, first and second openings of each said set are symmetrically spaced radially on said conduit surface wherein said openings are longitudinally positionable along the esophagus adjacent to the cardiac organ to receive cardiac sounds and wherein said electrode thereby is located between said sets so as to be usable for atrial-type cardiac stimulation.

2. A probe as claimed in claim 1, wherein the distal end of the conduit is closed and a fluid impermeable membrane overlies each said opening.

3. A probe as claimed in claim 1, wherein two electrodes are positioned on the exterior of the conduit between the longitudinal positions of the openings.

4. A probe as claimed in claim 3, wherein the electrodes are spaced apart longitudinally in the range of approximately 10-30 millimeters.

5. A probe as claimed in claim 4, wherein the conduit is cylindrical and the electrodes are hollow cylindrical sleeves which encircle the conduit in an interference fit.

6. A probe as claimed in claim 5, wherein there are two conductors each in electrical contact with a respective one of the electrodes, an end of each conductor extending through the wall of the conduit and being trapped between the electrode and the conduit in electrical contact with the electrode.

7. A probe as claimed in claim 4, wherein each opening is longitudinally spaced within approximately 25 millimeters of at least one electrode.

8. A probe as claimed in claim 1, further comprising a temperature sensor inside said conduit and an electrical conductor connected to said temperature sensor extending from said sensor to said proximal end for connection to a temperature read-out device.

9. An electrocardial probe comprising:
   a tubular conduit sized and shaped for insertion past the pharynx of a body, the conduit having a closed distal end to be inserted into the body and an open proximal end to be located exterior of the body;
   a pair of sets of openings, the openings in each set disposed circumferentially around the conduit, the two sets of openings being spaced from each other longitudinally along the conduit, each of the openings extending through the conduit;
   a pair of cylindrical conductive electrodes extending around the conduit, each of the electrodes positioned closely adjacent to a respective one of the two sets of openings, the electrodes being positioned between the sets of openings; and
   a pair of conductors extending inside of the conduit from the proximal end thereof to connect to the electrodes so that electrical stimulation can be applied between the electrodes and including flexible thin membranes fixed in place over the openings to prevent body fluids from flowing into the openings.

10. A probe as claimed in claim 9, wherein there are four openings in each set of openings.

11. A probe as claimed in claim 9, wherein the electrodes are spaced apart a distance of between 10 and 30 millimeters.

12. An electrocardial probe comprising:
   a tubular conduit sized and shaped for insertion past the pharynx of a body, the conduit having a closed distal end to be inserted into the body and an open proximal end to be located exterior of the body;
   a pair of sets of openings, the openings in each set disposed circumferentially around the conduit, the two sets of openings being spaced from each other longitudinally along the conduit, each of the openings extending through the conduit;
   a pair of cylindrical conductive electrodes extending around the conduit, each of the electrodes positioned closely adjacent to a respective one of the two sets of openings, the electrodes being positioned between the sets of openings;
   a pair of conductors extending inside of the conduit from the proximal end thereof to connect to the electrodes so that electrical stimulation can be applied between the electrodes; and a temperature sensor placed in the distal end of the conduit and connected with the proximal end of the conduit with conductive wires so that the temperature of the interior of the body can be readily monitored.

13. An electrocardial probe comprising:
   a tubular conduit sized and shaped for insertion past the pharynx of a body, the conduit having a closed distal end to be inserted into the body and an open proximal end to be located exterior of the body;
   a pair of sets of openings, the openings in each set are disposed circumferentially around the conduit, the two sets of openings being spaced from each other longitudinally along the conduit, each of the openings extending through the conduit;
   a pair of cylindrical conductive electrodes extending around the conduit, each of the electrodes is positioned closely adjacent to a respective one of the two sets of openings, the electrodes being positioned between the sets of openings; and
   a pair of conductors extending inside of the conduit from the proximal end thereof to connect to the electrodes so that electrical stimulation can be applied between the electrodes; and stomach feeding or pumping tubing located in the conduit.

14. A device insertable in part into an esophagus adjacent to a selected organ comprising:
   a flexible, elongated body having a proximal end and a distal end, said body defining an axially extending, internal lumen which extends, at least, adjacent to said distal end;
   first and second openings which extend through said body to said lumen, said openings being symmetrically and circumferentially disposed on said body, adjacent to said distal end;

third and fourth openings which extend through said body to said lumen, said third and fourth openings being symmetrically and circumferentially disposed on said body, displaced from said first and second openings toward said proximal end;

at least one electrode carried on said body between said first and second and said third and fourth openings and at least one conductor extending from said proximal end through said body to said electrode; and at least one flexible, thin membrane, transmissive of audible organ sounds, affixed to said body and covering said openings to exclude body fluids.

15. A device as in claim 14 including a temperature sensor carried at said distal end and at least one conductor extending from said proximal end, through said body to said sensor.